United States Patent
Kobayashi et al.

(10) Patent No.: US 9,758,766 B2
(45) Date of Patent: Sep. 12, 2017

(54) ARTIFICIAL KIDNEY PRECURSOR AND PROCESS FOR PRODUCTION THEREOF

(71) Applicants: Otsuka Pharmaceutical Factory, Inc., Naruto-shi (JP); Jichi Medical University, Shimotsuke-shi (JP); The Jikei University, Tokyo (JP); Tokyo Women's Medical University, Tokyo (JP)

(72) Inventors: Eiji Kobayashi, Wakayama (JP); Takashi Yokoo, Tokyo (JP); Koutaro Kai, Tokyo (JP)

(73) Assignees: OTSUKA PHARMACEUTICAL FACTORY, INC., Naruto-shi, Tokushima (JP); JICHI MEDICAL UNIVERSITY, Shimotsuke-shi, Tochigi (JP); THE JIKEI UNIVERSITY, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 119 days.

(21) Appl. No.: 14/565,104

(22) Filed: Dec. 9, 2014

(65) Prior Publication Data
US 2015/0104434 A1   Apr. 16, 2015

Related U.S. Application Data

(62) Division of application No. 13/001,764, filed as application No. PCT/JP2009/062098 on Jul. 2, 2009, now abandoned.

(30) Foreign Application Priority Data

Jul. 2, 2008   (JP) ................................ 2008-173935

(51) Int. Cl.
C12N 5/071     (2010.01)
A61K 35/22     (2015.01)
A61K 35/12     (2015.01)

(52) U.S. Cl.
CPC ............ *C12N 5/0697* (2013.01); *A61K 35/22* (2013.01); *C12N 5/0686* (2013.01); *A61K 35/12* (2013.01); *C12N 2502/02* (2013.01); *C12N 2506/1346* (2013.01); *C12N 2523/00* (2013.01)

(58) Field of Classification Search
None
See application file for complete search history.

(56) References Cited

U.S. PATENT DOCUMENTS

2004/0235161 A1   11/2004   Tabata et al.

FOREIGN PATENT DOCUMENTS

| CA | 2606983 A | 11/2006 |
|---|---|---|
| CA | 2676546 A1 | 11/2007 |
| CA | 2658060 A1 | 1/2008 |
| EP | 2014316 A | 1/2009 |
| RU | 2214280 C2 | 10/2008 |
| WO | 9300808 A1 | 1/1993 |
| WO | 09918195 A2 | 4/1999 |
| WO | 02061053 A1 | 8/2002 |
| WO | 2006/117889 A1 | 11/2006 |
| WO | 2007025233 A1 | 3/2007 |
| WO | 2007/125916 A1 | 11/2007 |
| WO | 2007/149861 A2 | 12/2007 |
| WO | 2008/004598 A1 | 1/2008 |

OTHER PUBLICATIONS

Rogers, S.A., et al., "Transplantation of Developing Metanephroi Into Adult Rats" Kidney International, 1988, vol. 54, p. 27-37.
Yokoo, T., et al., "Generation of a Transplantable Erythropoietin-Producer Derived from Human Mesenchymal Stem Cells", Transplantation, Jun. 15, 2008, vol. 85, No. 11, p. 1654-1658.
Yokoo, Takashi, "Novel Approaches for Therapeutic Kidney Regeneration", Japanese Journal of Clinical Medicine, Aug. 1, 2007, vol. 65, No. 8, pp. 1529-1537 (English abstract is enclosed).
Yokoo, T., et al., "Xenobiotic Kidney Organogenesis from Human Mesenchymal Stem Cells Using a Growing Rodent Embryo", J. Am. Soc. Nephrol., 2006, vol. 17, pp. 1026-1034.
International Search Report and Written Opinion, International Application No. PCT/JP2009/062098 dated Feb. 8, 2011.
Decision on Grant in Russian application, Application No. 2011103549 on Jul. 2, 2009. English translation enclosed.
Extended European Search Report in European Application No. 09773529.4, dated Oct. 17, 2013.
Hammerman, "Organogenesis of kidneys following transplantation of renal progenitor cells", Transplant Immunology, vol. 12, No. 3-4, pp. 229-239, 2004.
Matsumoto et al., "Xenotransplanted Embryonic Kidney Provides a Niche for Endogenous Mesenchymal Stem Cell Differentiation into Erythropoietin-Producing Tissue", Stem Cells, vol. 30, No. 6, pp. 1228-1235, 2012.
Nagashima, et al., "Production of Live Piglets following Cryopreservation of Embryos derived from in Vitro-Matured Ooctyes", Biology of Reproduction, vol. 76, No. 5, pp. 900-905, 2007.
Plotkin, et al., "Mesenchymal cells from adult kidney support angiogenesis and differentiate into mutliple interstitial cell types including erythropoietin-producing fibroblasts", American Journal of Physiology: Renal Physiology, vol. 291, pp. F902-F912, 2006.

(Continued)

*Primary Examiner* — David Berke-Schlessel
(74) *Attorney, Agent, or Firm* — Knobbe, Martens, Olson & Bear LLP

(57) ABSTRACT

The present invention provides an artificial kidney precursor containing a non-human mammalian metanephros separated out from a living body, wherein the metanephros has been subjected to freezing and thawing treatments outside a living body, and contains mammalian mesenchymal stem cells transferred outside a living body, and a method of production thereof.

4 Claims, No Drawings

(56) References Cited

OTHER PUBLICATIONS

Saito, et al., "Cryopreservation does not alter the allogenicity and development of vasculopathy in post-transplant rat aortas", Cryobiology, vol. 52, No. 2, pp. 251-260, 2006.

Tomita, et al., "Immune and Non-Immune factors in Crypreserved Tissues", The Journal of Heart and Lung Transplantation, vol. 22, No. 5, pp. 560-567, 2003.

Yokoo, Takashi and Kawamura, Tetsuya, "Xenobiotic kidney organogenesis: a new avenue for renal transplantation", Journal of Nephrology, vol. 22, No. 5, pp. 312-317, 2009.

Dekel, et al., "Human and porcine early kidney precursors as a new source for transplantation", Nature Medicine, Jan. 2003, vol. 9, No. 1, pp. 53-60.

Rogers, et al., "Prolingation of Life in Anephric Rats Following De Novo Renal Organogenesis", Organogenesis, 2004, vol. 1, Issue 1, pp. 22-25.

Chen, et al., "Development of New Organ Preservation Solutions in Kyoto University", Yonsei Medical Journal, 2004, vol. 45, No. 6, pp. 1107-1114.

Israeli Office Action issued in Israeli Patent Application No. 210,277 and English translation thereof—6 pages.

Arar, Mazen, et al., "Platelet-derived Growth Factor Receptor beta Regulates Migration and DNA Synthesis in Metanephric Mesenchymal Cells", The Journal of Biological Chemistry, 275, 9527-9533, 2000.

Bottemley, M.J. et al., "Preservation of Embryonic Kidneys for Transplantation", Transplantation Proceedings, 37, 280-284, 2005.

Wintour, E.M. et al., "The erythropoietin gene is expressed strongly in the mammalian mesonephric kidney", Blood, 88, 3349-3353, 1996.

Zang, et al., "The Morphometric Research of the Rat Embryonic Metanephroi Transplantation", Ryonei-Igakuin-Gakuhou, vol. 28, No. 2, pp. 16, 17 and 26, 2007.

Kokugai-Igaku, Rounen-Igaku-Bunastsu, "Bone Marrow Mesenchymal Stem Cells and Development thereof in Renal Diseases", School of Public Health, Jilin University (130021), vol. 29, No. 1, pp. 29-35, 2008.

Chinese Office Action issued on Jun. 13, 2012 for Chinese Application No. 200980126125.6.

ARTIFICIAL KIDNEY PRECURSOR AND PROCESS FOR PRODUCTION THEREOF

TECHNICAL FIELD

The present invention relates to an artificial kidney precursor and a method of production thereof.

BACKGROUND ART

The kidney is the major erythropoietin-producing organ; decreased erythropoietin production accompanying renal failure causes renal anemia as a complication.

In recent years, as next-generation therapeutic methods for renal anemia as such, methods have been proposed wherein an artificial kidney possessing a potential for erythropoietin production or a precursor thereof is produced by regenerative medical technology, and this is transplanted to renal anemia patients. For example, Patent Document 1 discloses a method for producing erythropoietin-producing organoid (artificial kidney) precursor comprising the step of transplanting isolated mesenchymal stem cell derived from a mammal into an embryo within a pregnant mammalian host or an embryo separated from a pregnant mammalian host to thereby induce the differentiation of the mesenchymal stem cell, wherein a site to which the mesenchymal stem cell is to be transplanted is a nephrogenic site of the embryo, and a timing of transplantation corresponds to the stage in which a immune system of the host is still immunologically tolerant.

In this method, however, there is a problem of complicated process because it is necessary to collect amniotic fluid from a pregnant mammal just before the artificial kidney precursor is transplanted to the patient, and confirm the biological safety of the precursor. Additionally, mesenchymal stem cells must be injected into an appropriate site in the embryo, that can become the kidney in the future; this operation requires high skills. Additionally, because mesenchymal stem cells must be injected into the embryo while the host's immune system is in a state of immune tolerance, the flexibility of the entire schedule of treatment is low. In this method, it is difficult to obtain a functional artificial kidney precursor unless whole embryo culture is performed; there arises a risk of contamination due to cultivation, and complicated process of purification after cultivation is necessary.

Hence, there is a demand for the development of a method of producing an artificial kidney precursor wherein 1) the biological safety of the artificial kidney precursor can easily be tested before transplantation to the patient, 2) the operation is simple, 3) flexibility of the entire schedule of treatment can be secured, and 4) no operation of cultivation is required.

PRIOR ART DOCUMENTS

Patent Document

Patent Document 1: WO 2008/004598

SUMMARY OF THE INVENTION

Technical Problem

It is an object of the present invention to provide a method of producing an artificial kidney precursor wherein 1) the biological safety of the artificial kidney precursor can easily be tested before transplantation to the patient, 2) the operation is simple, 3) flexibility of the entire schedule of treatment can be secured, and 4) no operation of cultivation is required.

Solution to Problem

The present inventors conducted extensive investigations to accomplish the above-described object; as a result, the inventors found that the above-described problems can be solved by using an artificial kidney precursor obtained by freezing and thawing a metanephros separated from an embryo, and transferring patient-derived mesenchymal stem cells into the thawed metanephros, and developed the present invention.

Accordingly, the present invention relates to the following.

[1] An artificial kidney precursor comprising a non-human mammalian metanephros separated out from a living body, wherein the metanephros has been subjected to freezing and thawing treatments outside a living body, and comprises mammalian mesenchymal stem cells transferred outside a living body.

[2] The artificial kidney precursor described in [1], wherein the metanephros is of a mammalian embryo in a stage where the expression of MHC is still immature.

[3] The artificial kidney precursor described in [1], wherein the precursor is capable of acquiring a potential for erythropoietin production when transplanted into an omentum of a mammal.

[4] A method of producing an artificial kidney precursor, comprising the steps of:
(I) freezing a mammalian metanephros separated out from a living body;
(II) thawing the frozen mammalian metanephros; and
(III) transferring mammalian mesenchymal stem cells into the metanephros outside a living body before the freezing (I) or after the thawing (II).

[5] The method described in [4], wherein the metanephros used in (I) is a metanephros separated out from a mammalian embryo in a stage where the expression of MHC is still immature.

[6] The method described in [4], wherein the artificial kidney precursor is capable of acquiring a potential for erythropoietin production when transplanted into an omentum of a mammal.

Effect of the Invention

Using the method of the present invention, the biological safety of an artificial kidney precursor can easily be tested before transplantation. Using the method of the present invention, it is possible to produce an artificial kidney precursor by simple operations. Using the method of the present invention, the entire schedule of treatment can be flexibly designed because a precursor of artificial kidney can be produced with desired timing by using a freeze-preserved metanephros. Furthermore, because the method of the present invention substantially obviates the need of an operation of cultivation, it involves no risk of contamination and does not need a complicated process of purification after cultivation.

DESCRIPTION OF EMBODIMENTS

The present invention provides an artificial kidney precursor comprising a mammalian metanephros separated out from a living body, wherein the metanephros has been subjected to freezing and thawing treatments outside a living body, and comprises mammalian mesenchymal stem cells transferred outside a living body.

In the present invention, an "artificial kidney" refers to a cellular organization, not a single cell, having a potential for erythropoietin production, which is a function the kidney possesses in nature. The "artificial kidney" in the present invention may not have the function of filtering waste materials and water in the blood and discharging urine. Each cell of the artificial kidney contacts with each other three-dimensionally except on its surface, the adjoining cells exchanging information via various intercellular junction, and can have a potential for erythropoietin production regulation.

A "precursor" refers to a tissue that turns into an artificial kidney when placed in a living body. Although the "precursor" has factors necessary for potentials for erythropoietin production and production regulation, it is in a state where the potentials for erythropoietin production and production regulation are not exhibited because of an environmental factor. The artificial kidney precursor is capable of acquiring a potential for erythropoietin production when transplanted to the omentum of a mammal.

A "potential for erythropoietin production regulation" means the capability of producing a large amount of erythropoietin (an amount required for amelioration of anemia) at times when a larger amount of erythropoietin than in a normal state is required in the body of the recipient (patient) (in anemia and the like), and producing an amount of erythropoietin required for retaining a normal state in the body at times when the recipient (patient) is in a normal state (anemia has been ameliorated and the like). That is, the artificial kidney of the present invention is advantageous over conventional erythropoietin-producing cells in that it is capable of producing an amount of erythropoietin required for the recipient (patient), and capable of producing erythropoietin continuously for a long time by taking necessary nutrients from blood vessels in the omentum.

In the present invention, a "metanephros" refers to a site corresponding to the genesis of the kidney in the mammalian embryo. The metanephros used in the present invention is preferably such that blast cells of the kidney are in a budding state before the start of development. The metanephros is located around the ureteric bud budding site in the mammalian embryo, more specifically between the somite and lateral plate. The metanephros is preferably the metanephrogenic mesoderm.

As examples of the mammal from which the metanephros is derived, laboratory animals such as rodents such as mice, rats, hamsters and guinea pigs, and rabbits; domestic animals such as pigs, bovines, goat, horses, sheep and minks; companion animals such as dogs and cats; primates such as humans, monkeys, rhesuses, marmosets, orangutans and chimpanzees; and the like can be mentioned. The mammal is preferably a rat or pig.

The metanephros is separated from a mammalian embryo outside the living body. As the embryo, one in which the expression of MHC (major histocompatibility complex) is still immature is suitably used. By using a metanephros in this stage, immune reactions accompanied by transplantation of an artificial kidney precursor to the recipient can be avoided. When the embryo is of a non-primate mammal, it is preferable that the metanephros be separated out in a stage before an exogenous antigen (carbohydrate antigen such as alpha-Gal) emerges. For example, in experiments using rats, embryo of normally E (stage embryonic day) 9 to 16, preferably E10 to 15, more preferably E11 to 14, is used. For other mammals as well, embryo in equivalent stages can suitably be used. However, preceding or following stages can also be applied, provided that conditions are chosen. Separation of a metanephros from an embryo can be performed using a stereomicroscope and the like.

Freezing treatment of a metanephros is performed in a cryopreservation liquid conventionally used to freeze mammalian tissue or cells. The cryopreservation liquid generally contains a cryopreservative such as DMSO, glycerin and the like. The concentration of the cryopreservative is normally in the range of 5 to 30% by weight, preferably 10 to 20% by weight. The preservation liquid may contain serum. The concentration of the serum is normally 5 to 50% by weight, preferably 10 to 30% by weight. As preferred cryopreservation liquids, the ET-KYOTO solution containing DMSO and FCS, CELLBANKER (registered trademark) and the like can be mentioned.

By freezing the metanephros, immune reactions accompanied by transplantation of the artificial kidney precursor to the recipient (patient) can be suppressed.

The frozen metanephros can be preserved in a frozen state nearly permanently, and can be used after being thawed and roused from the sleep as required. Temperature during cryopreservation is generally −80 to −200° C., preferably −196° C. (in liquid nitrogen). Because an artificial kidney precursor can be produced at desired timing due to cryopreservation of a metanephros, the entire schedule of treatment can be flexibly designed.

The frozen metanephros is subjected to thawing treatment in a physiological culture medium according to a conventional method. The method of thawing is not particularly limited; for example, with a freezing tube floating in a 37° C. thermoregulated bath, the frozen metanephros is thawed by adding dropwise the physiological culture medium thereto. For eliminating contamination of the cryopreservation liquid, the thawed metanephros is preferably washed with the physiological culture broth.

The metanephros used in the artificial kidney precursor of the present invention comprises mammalian mesenchymal stem cells transferred outside a living body.

"Mesenchymal stem cells" broadly mean a population of stem cells that proliferate in the undifferentiated state, and are capable of differentiating into all or some of osteoblasts, chondroblasts, lipoblasts and the like, or progenitor cells thereof. The mesenchymal stem cells used in the present invention possess a potential for differentiating into erythropoietin-producing cells of the kidney.

As examples of the mammal from which mesenchymal stem cells are derived, laboratory animals such as rodents such as mice, rats, hamsters and guinea pigs, and rabbits; domestic animals such as pigs, bovines, goat, horses, sheep and minks; companion animals such as dogs and cats; primates such as humans, monkeys, rhesuses, marmosets, orangutans and chimpanzees; and the like can be mentioned. The mammal is preferably a rat or human.

The mammal from which the mesenchymal stem cells are derived is preferably the same animal species as the recipient to which transplantation of the artificial kidney precursor of the present invention is intended. Most preferably, the recipient's own mesenchymal stem cells are used.

Mesenchymal stem cells can be collected from mammalian bone marrow fluid, peripheral blood, umbilical blood and the like by a publicly known ordinary method. For example, human mesenchymal stem cells can be isolated via cultivation and passage of hematopoietic stem cells and the like obtained by bone marrow aspiration (Journal of Autoimmunity, 30 (2008) 163-171).

Mesenchymal stem cells isolated from a living body can also be expanded in vitro while maintaining the differentiating potential thereof by carrying out adhesion culture in an appropriate medium. The mesenchymal stem cells thus expanded in vitro also fall within the scope of the present invention. As the medium, for example, DMEM, EMEM, RPMI-1640, F-12, α-MEM, MSC growing medium (Bio Whittaker) and the like are used. Culturing temperature is generally in the range of about 30 to 40° C., and is preferably about 37° C. The $CO_2$ concentration is generally in the range of about 1 to 10%, and is preferably about 5%. Humidity is generally in the range of about 70 to 100%, preferably about 95 to 100%. For maintaining a high differentiating potential, it is preferable that the cultivation do not extend over 2 to 5 passages or more.

Transfer of mesenchymal stem cells into a metanephros is performed before freezing, or after thawing the metanephros. For example, mesenchymal stem cells are injected into a metanephros using a micropipette and the like under a stereomicroscope. The number of cells transferred is determined as appropriate on the basis of the size of the metanephros and the like; generally about $10^4$ to $10^6$ (for example, $5 \times 10^4$) mesenchymal stem cells per rat metanephros are injected.

Although mesenchymal stem cells suspended in a physiological culture medium may be used for the transfer, mesenchymal stem cells enclosed in a gel containing an extracellular matrix component (laminin, collagen type IV, entactin, heparan sulfate proteoglycan, Matrigel (registered trademark) and the like) are suitably used from the viewpoint of prevention of leakage of intracellular fluid at the time of paracentesis after cryopreservation.

The size of the artificial kidney precursor of the present invention need not to be close to the size of the kidney, which is an erythropoietin-producing organ; a size 1/50 to 1/10 of that of the entire kidney is sufficient.

The artificial kidney precursor of the present invention can be produced by performing the following process:
(I) freezing a mammalian metanephros separated out from a living body;
(II) thawing the frozen mammalian metanephros; and
(III) transferring mammalian mesenchymal stem cells into the metanephros outside a living body before the freezing (I) or after the thawing (II).

The definitions of the respective terms and details of the operations are as described above.

Although the artificial kidney precursor of the present invention obtained by the above-described process may be subjected to organ culture, it is preferable that organ culture be not performed because there is no risk of contamination, and a complicated process of purification after cultivation is unnecessary. The artificial kidney precursor of the present invention is advantageous in that it is capable of acquiring adequate potentials for erythropoietin production and production regulation, when transplanted into a mammal, without being subjected to such a process of organ culture. The organ culture can be performed by placing the artificial kidney precursor on a filter, adding an appropriate medium to a dish thereunder, and allowing the dish to stand in an incubator.

When the artificial kidney precursor of the present invention is transplanted into a living body of a recipient mammal, the precursor engrafts in the recipient's body, and the mesenchymal stem cells contained in the precursor proliferate and differentiate into erythropoietin-producing cells of the kidney. As a result, the artificial kidney precursor differentiates into an artificial kidney possessing potentials for erythropoietin production and production regulation, which is now capable of producing erythropoietin in the living body continuously for a long time by taking necessary nutrients from blood vessels. Therefore, the artificial kidney precursor of the present invention is useful for the treatment of erythropoietin-related diseases. By transplanting the artificial kidney precursor of the present invention to a mammal, erythropoietin-related diseases in the mammal can be treated.

In the present invention, an "erythropoietin-related disease" is a disease associated with a reduction of the amount of erythropoietin produced, including anemias related to renal failure, diabetes, ulcers, cancers, infections, dialysis, surgery or chemotherapies. In particular, in case of anemia due to chronic renal failure, erythropoietin cannot be produced because of progressive destruction of renal parenchyma and liver function, so the erythropoietin concentration in the circulation does not rise; this is a major problem.

As examples of the recipient mammal, laboratory animals such as rodents such as mice, rats, hamsters and guinea pigs, and rabbits; domestic animals such as pigs, bovines, goat, horses, sheep and minks; companion animals such as dogs and cats; primates such as humans, monkeys, rhesuses, marmosets, orangutans and chimpanzees; and the like can be mentioned. The recipient mammal is preferably a rat or human.

Although the method of transplanting the artificial kidney precursor of the present invention into a mammal is not particularly limited, as far as the precursor can engraft in the recipient's body and acquire potentials for erythropoietin production and production regulation, the artificial kidney precursor is preferably transplanted into the recipient mammal's omentum. Transplantation into the omentum can be performed by an ordinary surgical procedure; for example, a method comprising picking up the tissue to be transplanted with a sharp forceps, making a small incision on the surface of the adipose tissue in the omentum with the forceps tip, and embedding the tissue in the incision, can be mentioned. The artificial kidney precursor of the present invention can also be transplanted into the omentum by means of an endoscope.

The dose of the artificial kidney precursor of the present invention varies depending on the subject of administration, target disease, symptoms and the like; generally, an artificial kidney precursor prepared from a swine metanephros is transplanted into an adult human renal anemia patient (a 60 kg body weight assumed), it is convenient to transplant about 10 metanephroses in one time of surgery, and to increase the number of metanephroses step by step while monitoring the severity of the patient's anemia, if required. In case of other animals, an amount calculated per 60 kg body weight can be transplanted.

The present invention is hereinafter described more specifically by means of the following Example, to which, however, the invention is never limited in any way.

Example

Metanephroses were separated from rat embryos at day 14 of gestation, and then cryopreserved in ET-Kyoto+10% DMSO+20% FCS. The diameters were about 2 mm.

After cryopreservation for 2 days, the frozen metanephroses were thawed. Rat mesenchymal stem cells were enclosed in Matrigel, and injected into the metanephroses at $1 \times 10^4$ cells per metanephros. Thereafter, the metanephroses were transplanted to the omenta of syngenic rats.

Seven days after the transplantation, the grown metanephroses were separated from the rats having received the metanephros transplants. The number of animals having received the metanephros transplants was 2, in each of which three and six, respectively, out of seven metanephroses, grew. The metanephroses grew to diameters of 6 to 8 mm. Erythropoietin production in the grown artificial kidney precursors was confirmed by the same method as that described in Transplantation VOL85, Noll, Jun. 15 2008, i.e., immunostaining and genetic analysis of erythropoietin-producing cells.

INDUSTRIAL APPLICABILITY

Using the method of the present invention, the biological safety of an artificial kidney precursor can easily be tested before transplantation. Using the method of the present invention, it is possible to produce an artificial kidney precursor by simple operations. Using the method of the present invention, the entire schedule of treatment can be flexibly designed because a precursor of artificial kidney can be produced with desired timing by using a freeze-preserved metanephros. Furthermore, because the method of the present invention substantially obviates the need of an operation of cultivation, it involves no risk of contamination and does not need a complicated process of purification after cultivation.

This application is based on a patent application No. 2008-173935 filed in Japan (filing date: Jul. 2, 2008), the contents of which are incorporated in full herein by this reference.

What is claimed is:

1. A method of producing an artificial kidney precursor that is to be transplanted to a human recipient, the precursor comprising:
    a non-human mammalian metanephros comprising blast cells of a kidney; and
    human mesenchymal stem cells isolated from the human recipient, which method comprises the steps of:
    (I) freezing the non-human mammalian metanephros comprising blast cells of a kidney, said metanephros being separated out from a non-human mammalian embryo outside the living body;
    (II) thawing the frozen mammalian metanephros; and
    (III) transferring said human mesenchymal stem cells into the metanephros comprising blast cells of a kidney, outside the living body of the non-human mammalian embryo after the thawing (II), thereby obtaining the artificial kidney precursor.

2. The method according to claim 1, wherein the metanephros used in (I) is a metanephros separated out from a non-human mammalian embryo in a stage where the expression of WlC is still immature.

3. The method according to claim 1, wherein the artificial kidney precursor is capable of acquiring a potential for erythropoietin production when transplanted into an omentum of the human recipient.

4. The method according to claim 1, further comprising transplanting the obtained artificial kidney precursor into the human recipient.

* * * * *